(12) United States Patent
Collery (10) Patent No.: US 11,998,158 B2
(45) Date of Patent: Jun. 4, 2024

(54) PATIENT EXCRETION COLLECTION DEVICES

(71) Applicant: Thomas Joseph Collery, Oyster Bay, NY (US)

(72) Inventor: Thomas Joseph Collery, Oyster Bay, NY (US)

( * ) Notice: Subject to any disclaimer, the term of this patent is extended or adjusted under 35 U.S.C. 154(b) by 232 days.

(21) Appl. No.: 17/379,729

(22) Filed: Jul. 19, 2021

(65) Prior Publication Data

US 2022/0015591 A1 Jan. 20, 2022

Related U.S. Application Data

(60) Provisional application No. 63/053,715, filed on Jul. 20, 2020.

(51) Int. Cl.
| | | |
|---|---|---|
| *A47L 7/00* | (2006.01) | |
| *A47L 5/36* | (2006.01) | |
| *A47L 9/00* | (2006.01) | |
| *A47L 9/14* | (2006.01) | |
| *A47L 9/24* | (2006.01) | |
| *A61B 10/00* | (2006.01) | |

(52) U.S. Cl.
CPC ............. *A47L 7/0085* (2013.01); *A47L 5/365* (2013.01); *A47L 7/0023* (2013.01); *A47L 7/0071* (2013.01); *A47L 7/008* (2013.01); *A47L 9/0072* (2013.01); *A47L 9/1409* (2013.01); *A47L 9/24* (2013.01); *A61B 10/0038* (2013.01); *A61B 10/007* (2013.01)

(58) Field of Classification Search
CPC ...... A47L 7/0085; A47L 5/365; A47L 7/0023; A47L 7/0071; A47L 7/008; A47L 9/0072; A47L 9/1409; A47L 9/24; A47L 5/38; A47L 7/0028; A61B 10/0038; A61B 10/007; A61M 2202/068; A61M 1/60; A61M 1/78; A61M 1/87; A61F 5/451; A61F 5/4407; A61F 5/4405; A61F 5/44

See application file for complete search history.

(56) References Cited

U.S. PATENT DOCUMENTS

| 2,867,835 | A | | 1/1959 | Brown, Jr. et al. | |
|---|---|---|---|---|---|
| 3,533,109 | A | * | 10/1970 | Masakichi | A61G 9/006 4/144.1 |
| 3,866,264 | A | | 2/1975 | Engquist | |
| 4,050,103 | A | | 9/1977 | Nakao et al. | |
| 4,345,342 | A | * | 8/1982 | Saito | A61G 9/006 604/347 |
| 4,360,933 | A | * | 11/1982 | Kimura | A61F 5/451 4/144.1 |

(Continued)

FOREIGN PATENT DOCUMENTS

| DE | 19619597 A1 * 11/1997 | A61F 5/451 |
|---|---|---|
| TW | M531268 U * 11/2016 | |

(Continued)

*Primary Examiner* — Susan S Su
*Assistant Examiner* — Ted Yang
(74) *Attorney, Agent, or Firm* — Daniel P. Burke & Associates, PLLC; Daniel P. Burke (57) ABSTRACT

Devices for collecting patient excretions utilize existing suction sources and facilitate the cleaning of bedding and/or a patient. Patient excretion collection devices comprise a collection reservoir and a collection wand which are attached to an existing source of suction.

15 Claims, 7 Drawing Sheets

(56) References Cited

U.S. PATENT DOCUMENTS

| | | | | |
|---|---|---|---|---|
| 4,631,061 A | * | 12/1986 | Martin | A61F 5/451 604/323 |
| 5,002,541 A | * | 3/1991 | Conkling | A61F 5/44 604/324 |
| 5,280,666 A | | 1/1994 | Wood et al. | |
| 5,647,090 A | | 7/1997 | Yang | |
| 5,678,564 A | * | 10/1997 | Lawrence | A61F 5/455 600/573 |
| 5,685,864 A | * | 11/1997 | Shanley | A61B 5/150244 604/207 |
| 5,771,531 A | * | 6/1998 | Swartz | A47L 5/24 15/344 |
| 5,894,608 A | * | 4/1999 | Birbara | A61F 5/4556 604/319 |
| 6,093,168 A | * | 7/2000 | Mendenhall | A61M 1/062 604/74 |
| 6,311,339 B1 | * | 11/2001 | Kraus | A61G 9/006 4/144.1 |
| 6,904,621 B2 | | 6/2005 | Otto et al. | |
| 7,404,230 B1 | | 7/2008 | Phillips | |
| 7,513,894 B2 | * | 4/2009 | Howlett | A61G 9/00 604/327 |
| 9,782,048 B2 | | 10/2017 | Witter et al. | |
| 10,292,557 B2 | | 5/2019 | Latimer | |
| 2002/0087131 A1 | * | 7/2002 | Wolff | A61B 5/20 604/327 |
| 2003/0192816 A1 | | 10/2003 | Opfel | |
| 2004/0176746 A1 | * | 9/2004 | Forral | A61F 5/453 604/544 |
| 2004/0187200 A1 | * | 9/2004 | Otto | A61F 5/451 4/144.1 |
| 2004/0236292 A1 | * | 11/2004 | Tazoe | A61F 5/451 604/317 |
| 2005/0015916 A1 | | 1/2005 | Orubor | |
| 2005/0038374 A1 | * | 2/2005 | Williams, Jr. | A61M 1/84 604/20 |
| 2006/0015080 A1 | | 1/2006 | Mahnensmith | |
| 2007/0277343 A1 | * | 12/2007 | Reiling | A47L 5/24 15/344 |
| 2011/0064586 A1 | * | 3/2011 | Matsumiya | A61G 9/006 417/36 |
| 2012/0253303 A1 | * | 10/2012 | Suzuki | A61F 13/42 374/45 |
| 2021/0127938 A1 | * | 5/2021 | Mallon | A47L 9/2847 |
| 2021/0267787 A1 | * | 9/2021 | Nazemi | A61M 1/71 |
| 2022/0142843 A1 | * | 5/2022 | Tourchak | A61M 1/60 |
| 2022/0409422 A1 | * | 12/2022 | Schneider | A61F 5/4404 |

FOREIGN PATENT DOCUMENTS

| | | | | |
|---|---|---|---|---|
| WO | WO-2005060558 A2 | * | 7/2005 | A61G 9/00 |
| WO | 2017040839 A1 | | 3/2017 | |
| WO | WO-2023018657 A1 | * | 2/2023 | |

* cited by examiner

PATIENT EXCRETION COLLECTION DEVICES

RELATED APPLICATION DATA

This application claims the benefit of U.S. Provisional Patent Application Ser. No. 63/053,715 filed on Jul. 20, 2020, and which is hereby incorporated by reference.

Devices for collecting patient excretions utilize existing suction sources and facilitate the cleaning of bedding and/or a patient. The disclosed devices comprise a collection container and a collection wand which are attached to an existing source of suction.

BACKGROUND

Patients in hospitals and other health care institutions require constant care and vigilance. One of the least desirable and time consuming, yet very important, tasks required of nurses and other care givers is cleaning up patient excretions, such as loose stool and vomit, from bedding and from the patients themselves. Traditional methods of cleaning up bedding and patients use copious amounts of soap, wipes, towels, bedding, gowns and absorbent patient pads. It would be desirable to provide a quicker and more efficient manner of cleaning and collecting loose and liquid feces and other liquids excreted by a patient.

SUMMARY

Patient excretion collection devices utilize existing suction sources and facilitate the rapid cleaning of patient excretions from hospital bedding and/or from a patient. The disclosed devices comprise a collection container with at least one upper head portion, a lower body portion and an intermediate neck portion which connects the at least one head portion and body portion. The collection container and a collection wand are attached to an existing source of suction.

A vacuum port and an excretion inlet port are located in at least one upper head portion of the container. The container configuration and location of the ports require the collected patient excretions to pass downwardly after entering the excretion inlet port, into the body portion. The vacuum port is spaced from and above the body portion to minimize the risk of patient excretions exiting the collection container through the vacuum port.

In a preferred, illustrated embodiment, the vacuum port and excretion inlet port are located in spaced relation in the same forward wall of a single collection container head portion. In this illustrated embodiment, an internal wall separates the left side of the head and neck portions from the right side of the head and neck portions. The internal wall causes the vacuum to draw incoming patient excretions downwardly into the body portion of the collection container. Since the vacuum port is spaced from and above the body portion, the risk of patient excretions exiting the collection container through the vacuum port is minimized.

Another aspect includes the provision of a pivotal vacuum stopper plug which blocks patient excretions from exiting the collection container if the container is rotated beyond a certain predetermined angle.

DETAILED DESCRIPTION

The illustrated patient excretion collection devices illustrated in the drawings are light weight and portable to facilitate use by hospital personal and are relatively inexpensive to manufacture and are intended to be disposable.

Figure 1:
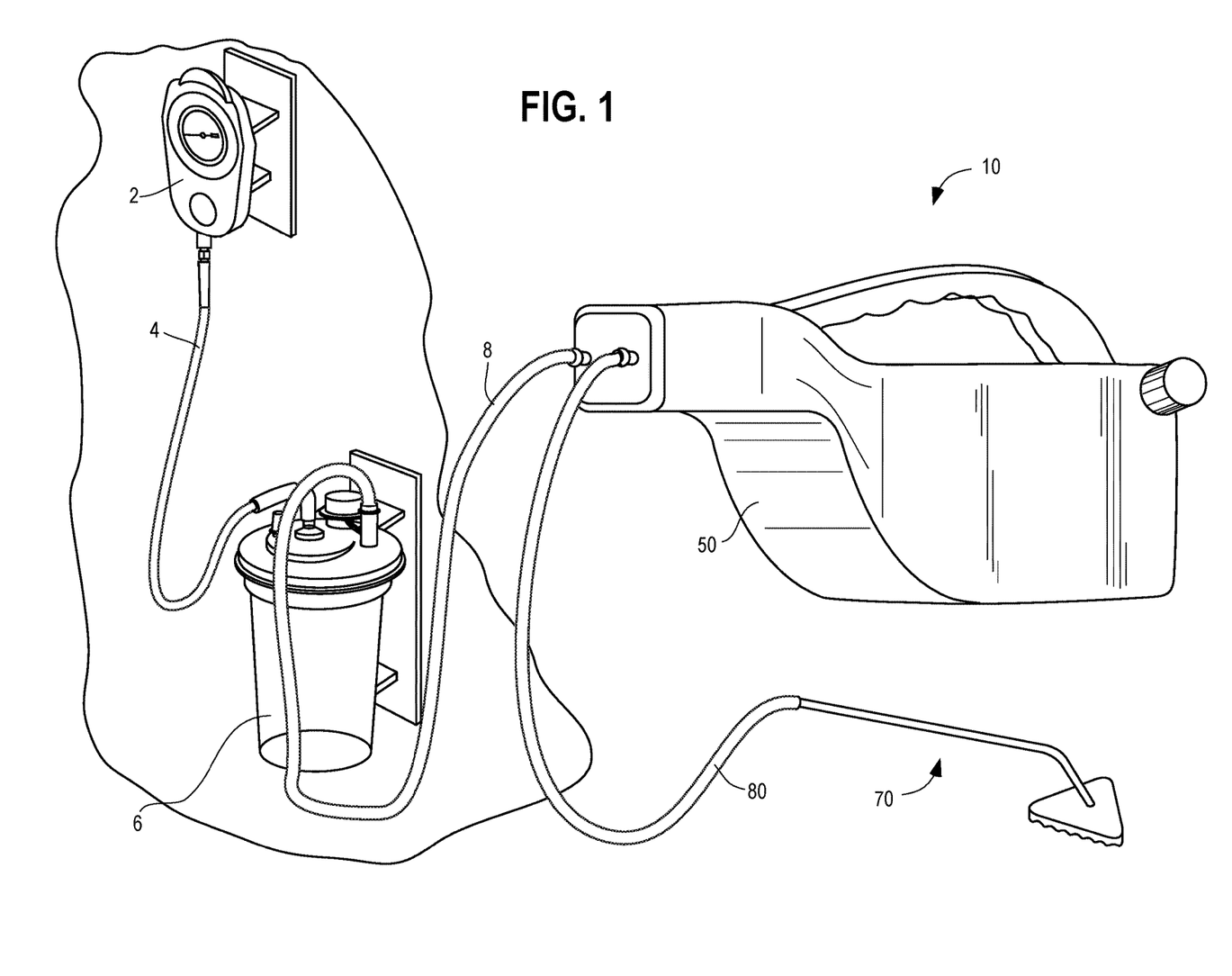
FIG. 1 is a perspective view of one embodiment of a collection device attached to a conventional hospital vacuum system.

FIG. 1 illustrates a first embodiment of a patient excretion collection device connected to a known hospital vacuum system. The known hospital vacuum system comprises a suction gauge 2 plugged into a centralized source of vacuum (not shown) and connected via an air hose 4 to a trap 6. The vacuum gauge 2 and trap 6 are mounted on a wall in a manner typically found in U.S. hospitals. Such vacuum systems typically include a control on the vacuum gauge for adjusting the strength of the vacuum.

This illustrated patient excretion collection device comprises a first hose 8, a collection container 10 and a wand 70 connected to the collection container 10 via a second hose 80. A handle 45 is provided on the top of collection container 10 to facilitate handling.

Figure 2:
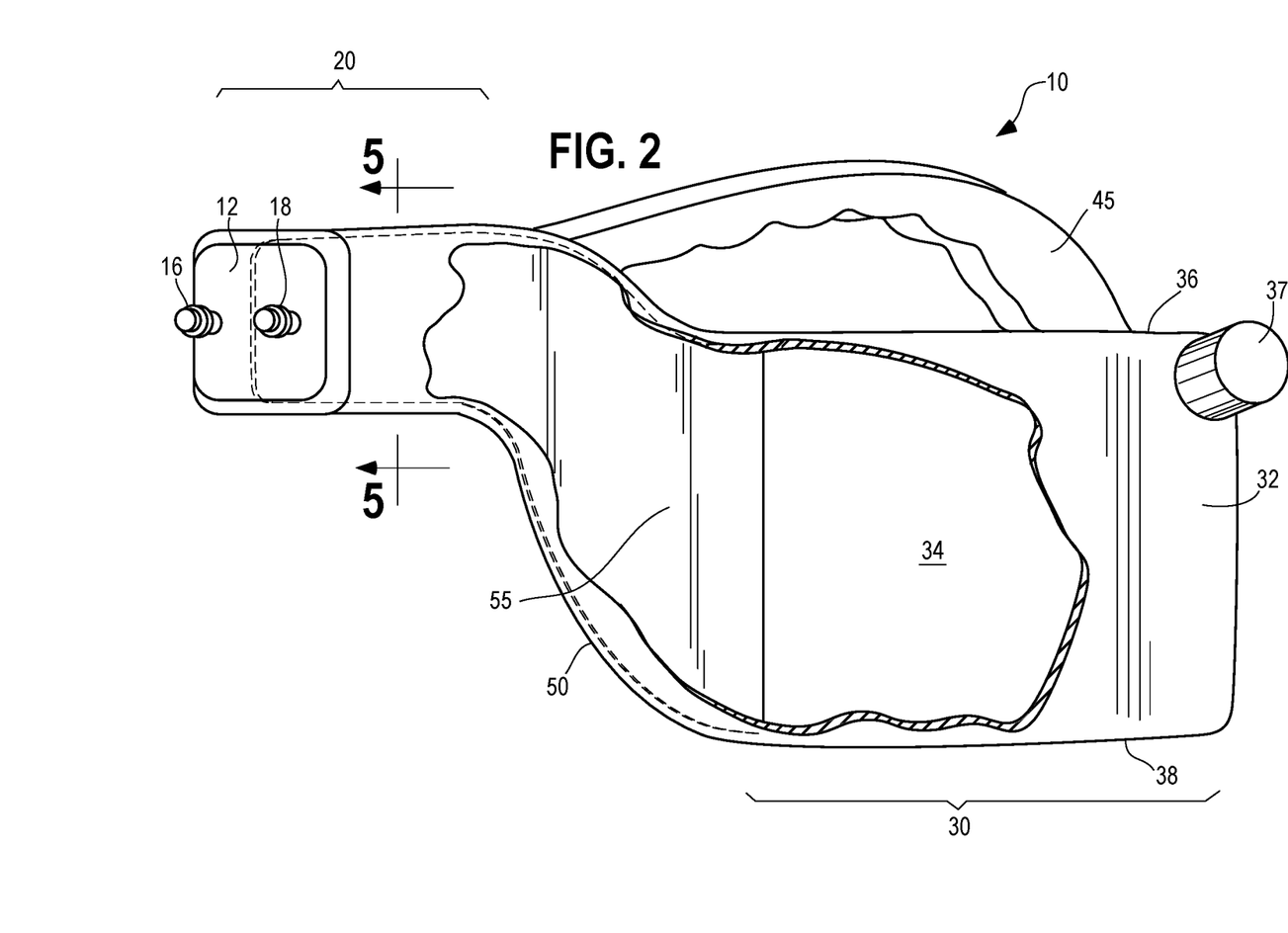
FIG. 2 is perspective view with sections removed of the portable collection container shown in FIG. 1.
Figure 3:
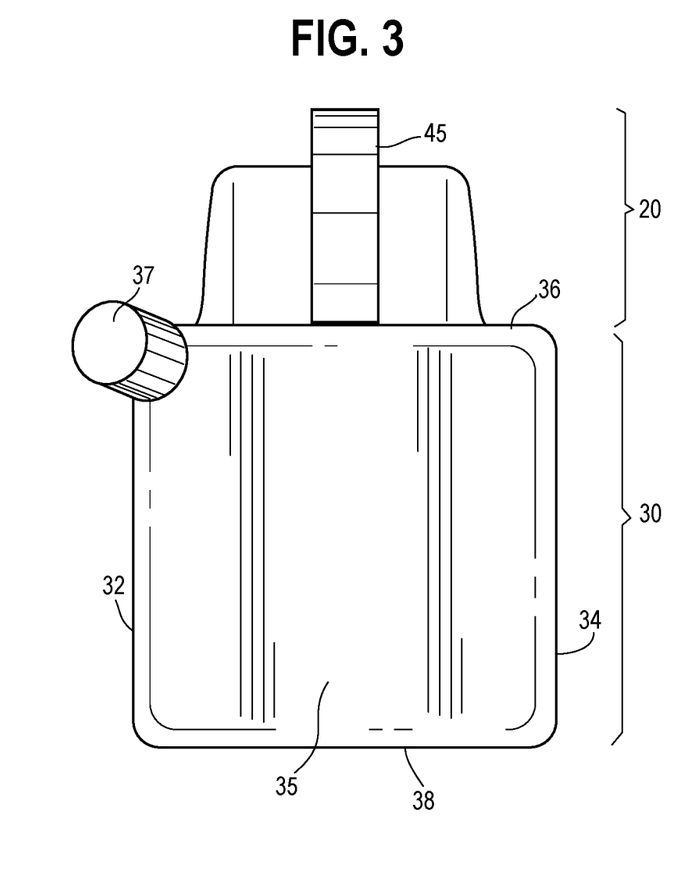
FIG. 3 is a rear view of the portable collection container shown in FIG. 1.

With reference to FIGS. 2-3, the illustrated collection container 10 comprises a rear, lower base portion 30 and a forward, upper head portion 20. The head portion 20 is connected to the base portion 30 by a sloping neck portion 50. As best shown in FIG. 3, the base portion 30 is narrower than head portion 20. The relative dimensions of the base portion 30 and head portion 20 enhance the stability of the collection container 10 by making it less likely that the collection container 10 will roll over during use, for example, if the container is placed on a bed during use.

The illustrated collection container 10 comprises three openings, namely a vacuum port 16, an excretion inlet port 18 and a sample port 39 which is covered by sample cap 37 in FIGS. 1-3. With the exception of these three openings, the collection container 10 is a sealed container defined by front wall 12, rear wall 35, left wall 32, right wall 34, bottom wall 38 and upper wall 36. Vacuum port 16 and excretion inlet port 18 in this illustrated embodiment pass through forward wall 12 and are positioned in horizontally spaced relation to each other. For example, the ports may be space by 1 or 2 inches. Both the vacuum port 16 and excretion inlet port 18 are provided with connectors in the form of two half-curved ridges which facilitate the placement of a hose over the connectors and the avoidance of the unintended disconnection of the hose during use. Prior to use, the vacuum port 16 is connected to a source of vacuum via hose 8 and the excretion inlet port 18 is connected to a collection wand via hose 80, in the manner depicted in FIG. 1.

Collection container 10 is also provided with an internal wall 55. In the illustrated embodiment, the internal wall 55 is positioned interiorly in the head and neck portions of the collection container and extends partially into the base portion. The forward end of the internal wall 55 abuts the interior of forward wall 12 between the internal openings of vacuum port 16 and excretion inlet port 18. Internal wall 55 extends from the interior of the upper wall 36 to the interior of lower wall 38.

During use of the collection device, a vacuum is applied to vacuum port 16 which results in a suction being applied at the inlet of the wand. This draws air and other material proximate the wand inlet into the collection container. It will be appreciated that the internal wall 55 causes vacuum drawn air and patient excretions to enter excretion inlet port 18, pass down the left side of neck portion 50 into the base portion 30 of collection container 10. Air will then be drawn back upwardly through the right side of neck portion 50 and out vacuum port 16. The strength of the vacuum is preferably adjusted so that when solids and/or liquid patient excretions are drawn into collection container 10, the weight of the liquids and solids and the distance between the internal opening in front wall 12 defined by vacuum port 16 and the patient excretions in the body portion will prevent the patient excretions from being drawn upwardly from the base portion of collection container through the vacuum port 16.

The disclosed patient excretion collection device allows a nurse or hospital attendant to vacuum up a mess of patient excretions very quickly from a bed and/or from a patient's body and clean the patient with minimal use of extra bedding and wipes.

Figure 4:
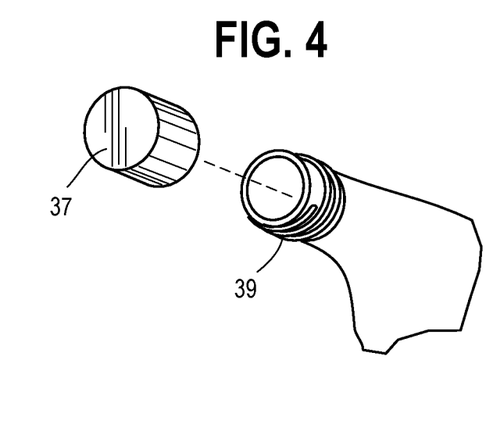
FIG. 4 is an exploded view of the sample port and cap of the portable collection container shown in FIG. 1.

The collection container 10 is provided with a sample port 39. The illustrated sample port has external threads for receiving a threaded cap 37. If a sample of the patient's excretion is desired, for example for laboratory analysis, the sample can be poured or otherwise removed through sample port 39.

Figure 5:
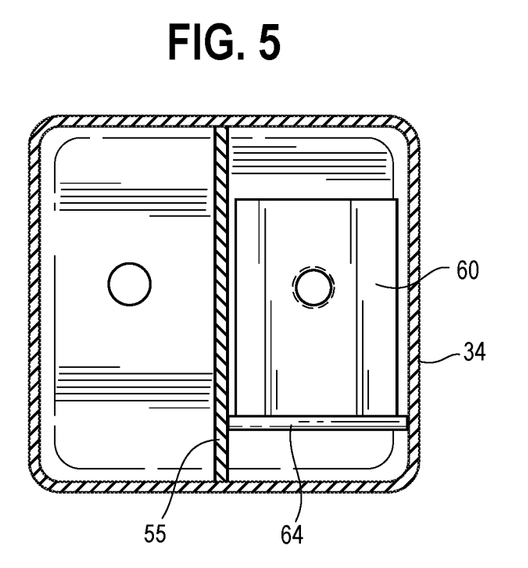
FIG. 5 is a rear view of the front connector wall of the portable collection container shown in FIG. 1 taken along lines 5-5 of FIG. 2.
Figure 6:
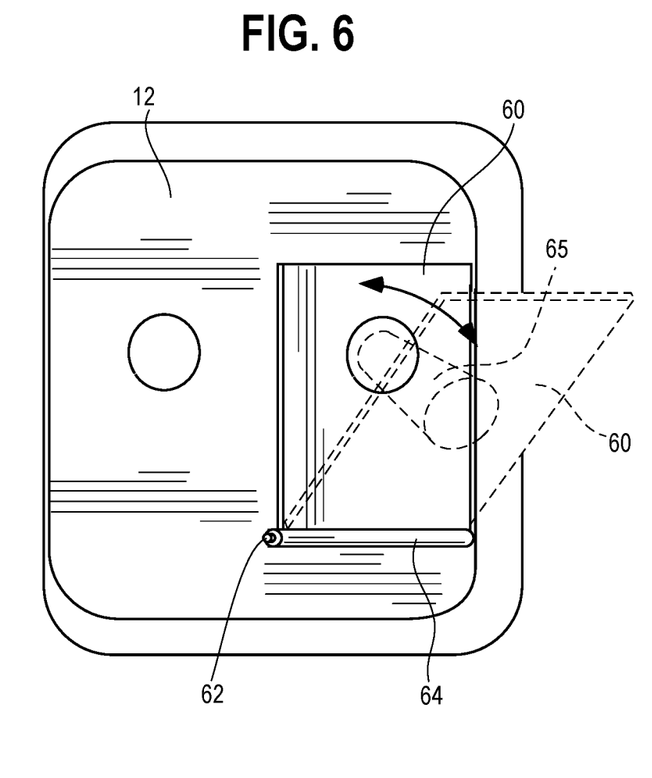
FIG. 6 is a partial, rear view of the front connector wall shown in FIG. 1 illustrating the rotation of the vacuum stopper flap.
Figure 7:
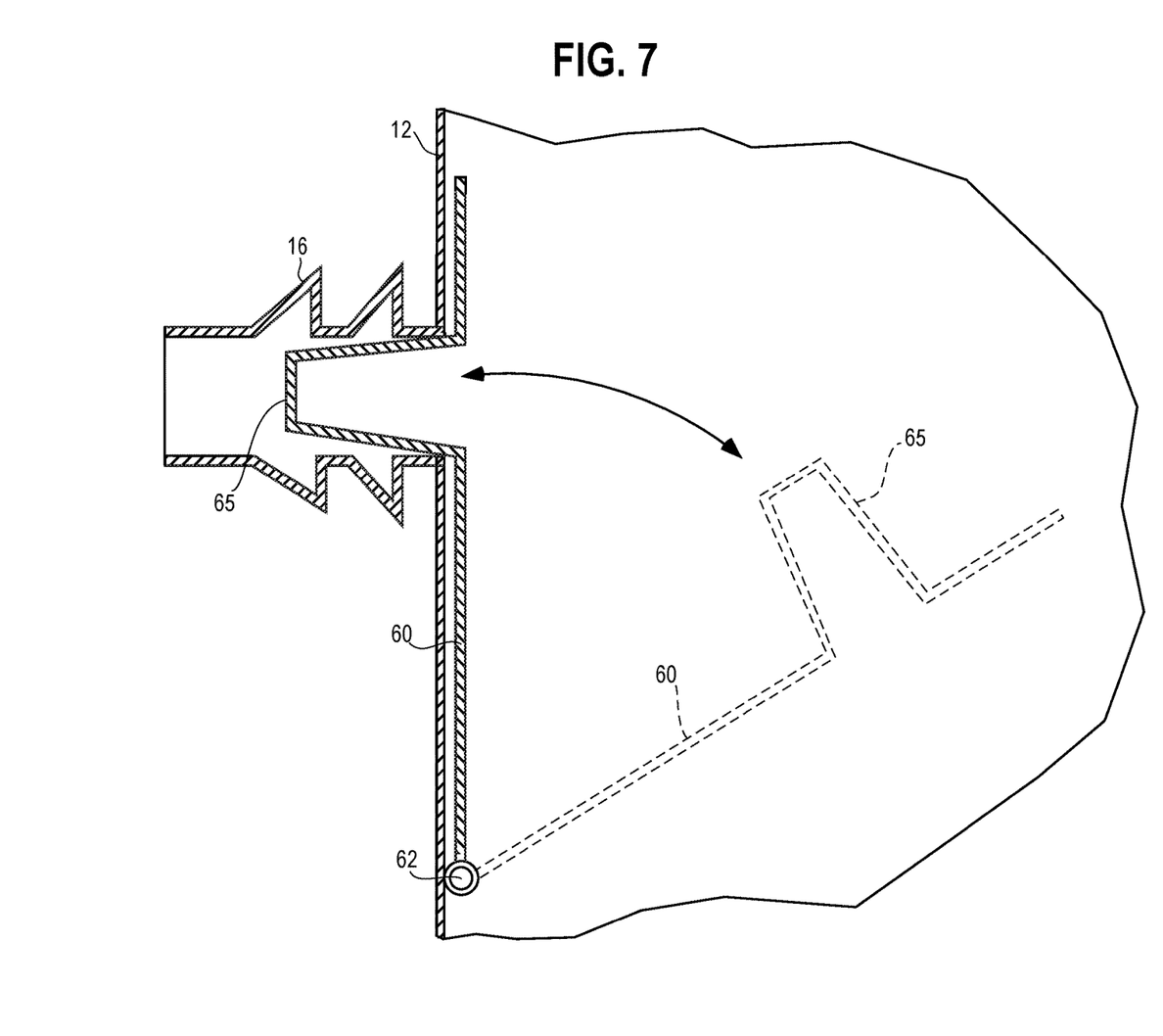
FIG. 7 is a partial, side view of the front connector wall of the portable container shown in FIG. 1 illustrating the rotation of the vacuum stopper flap.

Other than during the intentional collection of a patient's sample, it is presently believed that it is desirable to maintain all patient excretions within the collection container 10 after those excretions have been drawn in through excretion inlet port 18. It will be appreciated by nurses and others working in hospital environments that patient movement or other exigencies may cause collection container 10 to be knocked over or undesirably rotated during use. In order to prevent patient excretions from being drawn into the hospital's centralized vacuum system, the collection container 10 is provided with a vacuum stopper plug 65 designed to block the interior opening of vacuum port 16 when the collection container is rotated beyond, i.e. more than, a predetermined angle. FIG. 5 is a rear view of front wall 12 when stopper plug 65 is positioned to block vacuum port 16. FIG. 6 is a partial view of the interior of front wall 12 with the internal wall 55 removed for clarity. FIG. 7 is a cross-sectional view of the right side of front wall 12 showing vacuum port 16 and the stopper plug 65 positioned in the normally unobstructing position in phantom and in the blocking position in solid lines.

With reference to FIGS. 5-7, a tapered stopper plug 65 is positioned on a pivotal flap 60. Pivotal flap 60 is connected to internal wall 55 and right wall 34 by pins 62 which engage a hinge 64 of pivotal flap 60. Hinge 64 and pins 62 define a pivotal axis. Pivotal flap 60 normally rests in an open position with the stopper plug 65 spaced from the internal opening of vacuum port 16. Pivotal flap 60 can normally rest in an open position which is horizontal or which is inclined as shown by the dashed lines in FIG. 7. When collection container 10 is rotated sufficiently (in the counter-clockwise direction in FIG. 7), pivotal flap 60 and vacuum stopper plug 65 will rotate around the pivotal axis to cause stopper plug to block the internal opening of vacuum port 16, i.e. to the position depicted by the solid lines in FIG. 7. The vacuum being applied by the vacuum source will assist in drawing stopper plug 65 further into vacuum port 16 to more securely seat the stopper plug 65. The predetermined angle, beyond which the stopper plug 65 will pivot into the vacuum port 16, is determined by the relative angle of the stopper plug 65 and/or its supporting structure when in the open, i.e. unobstructing, orientation to the plane of the internal opening of vacuum port 16. For example, if the pivotal flap 60 is normally oriented 90 degrees from the plane of the internal opening of vacuum port 16 when in the unobstructing orientation, then rotation beyond 90 degrees will be required to cause the pivotal flap 60 to rotate sufficiently to locate the stopper plug 65 in the vacuum port 16. Similarly, if the pivotal flap 60 is normally oriented at a lesser angle to the plane of the internal vacuum port opening when in the unobstructing orientation, such as 45 degrees, then rotation beyond that lesser angle, e.g. 45 degrees, will be required to cause the pivotal flap 60 to rotate sufficiently to locate the stopper plug 65 in the vacuum port.

Figure 8:
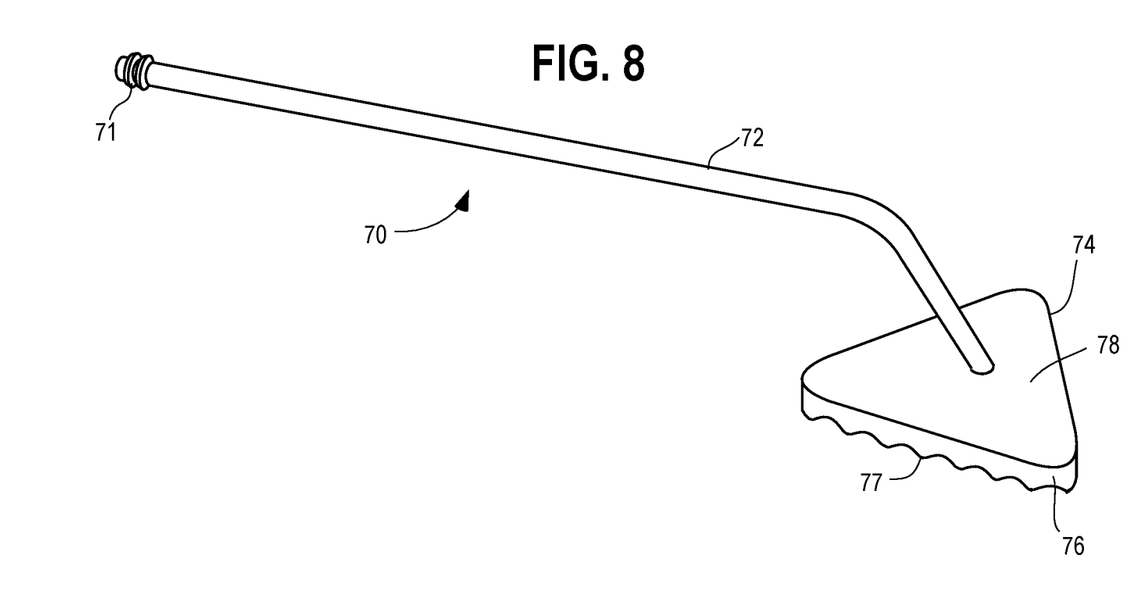
FIGS. 8 and 9 are perspective and bottom views, respectively, of the collection wand shown in FIG. 1.
Figure 9:
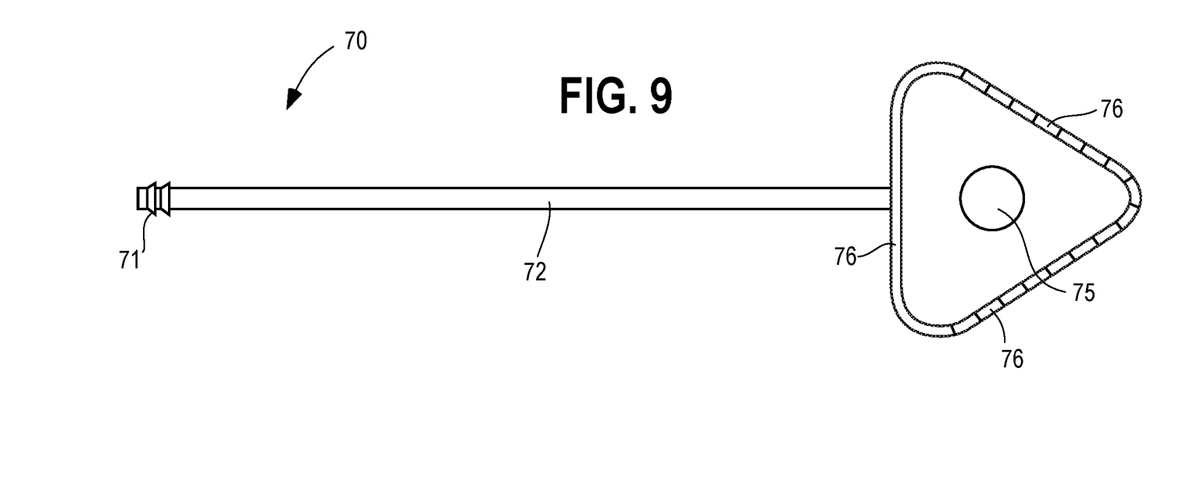

FIGS. 8 and 9 are top perspective and bottom views, respectively, of the collection wand 70 shown in FIGS. 1-7. This illustrated wand has a proximal hose connector 71, a hollow handle 72 and a wand head having an upper surface 78, side walls 76 having scalloped lower edge 77 and a suction inlet 75. The scalloped lowered edges are designed to minimize the likelihood of wet bed sheets or the patient's skin from forming an air tight seal with the wand head and thereby blocking the flow of air and excretions into the wand.

Figure 10:
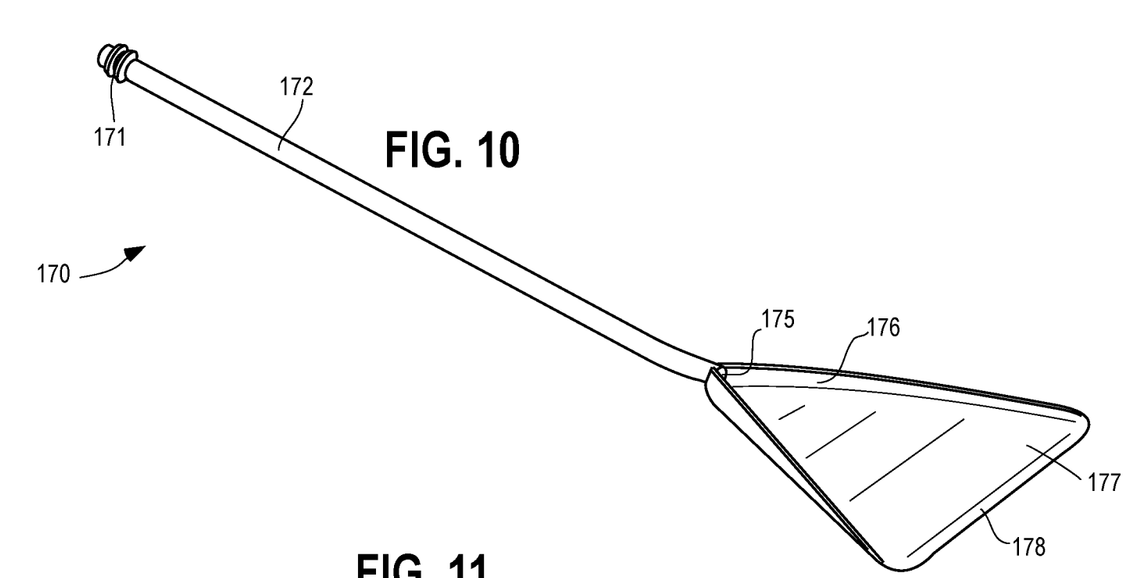
FIGS. 10 and 11 are perspective and bottom views, respectively, of another collection wand.
Figure 11:
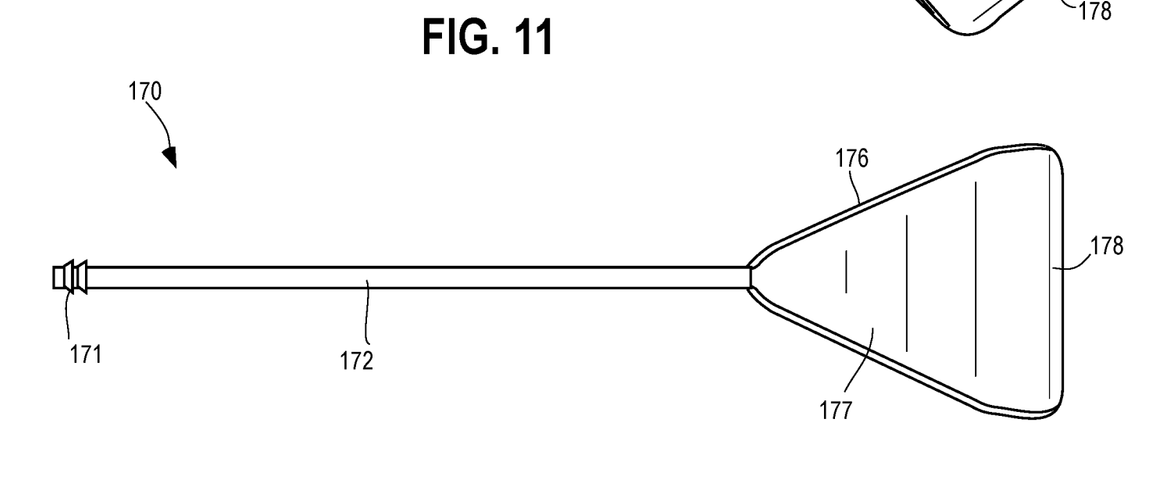

FIGS. 10 and 11 are top perspective and bottom views, respectively, of an alternative collection wand 170. This illustrated collection wand 170 has a proximal hose connector 171, a hollow handle 172, and a wand head. This wand head is generally in the form of a shallow shovel with a vacuum inlet 175, tapering side walls 176, a generally triangular bottom 177 and a beveled lower front edge 177. The beveled forward edge 177 and tapering sidewalls 176 of collection wand 170 are designed to allow a user to scoop patient excretions and guide them into vacuum inlet 175.

The wands are preferably light weight and small, e.g. about 9 to about 14 inches long in their entireties and the head is preferably small, e.g. length and width of about 1 inch each, to facilitate cleaning in small spaces. The disclosed embodiments show a relatively inexpensive patient excretion collection device which does not rely on an internal source of vacuum, is portable, disposable and provides a time saving alternative to a particularly undesirable task performed by busy nurses and other hospital personnel many times per day throughout the world.

The invention claimed is:

1. A collection device for use in collecting patient excretions comprising:
   a first hose comprising a first end and a second end;
   a collection container comprising a substantially enclosed interior; an upper head portion comprising a forward portion; a rear, lower base portion comprising a rear wall; a vacuum port, an excretion inlet port, and a handle;

said excretion inlet port positioned in said forward portion of said upper head portion;

at least one interior wall extending within the interior of said substantially enclosed interior from said forward portion of said upper head portion and rearwardly at least 25% of a distance from said excretion inlet port to said rear wall, said interior wall forming an internal baffle between said excretion inlet port and said vacuum port;

a selectively openable and sealable sample access port for taking excretion samples from said interior:

said first end of said first hose connected to a vacuum source and said second end of said first hose connected to said vacuum port;

a collection wand comprising a rear hose connector and a forward inlet; and a second hose comprising a first end and a second end, said first end of said second hose connected to said excretion inlet port and said second end of said second hose connected to said rear hose connector of said collection wand.

2. A collection device according to claim 1 further comprising a pivotal vacuum stopper flap comprising a vacuum port plug positioned proximate said vacuum port, wherein said vacuum port plug moves to block said vacuum port when said collection device is rotated beyond a certain predetermined angle.

3. A collection device according to claim 2 wherein said predetermined angle is 90 degrees.

4. A collection device according to claim 2 wherein said vacuum port plug moves to a position wherein at least a portion of said vacuum port plug is disposed in said vacuum port.

5. A collection device according to claim 1 wherein said lower base portion is wider than said forward portion.

6. A collection device according to claim 1 wherein said vacuum port is positioned higher than said base portion.

7. A collection device according to claim 1 wherein said vacuum port is positioned in said forward portion of said upper head portion on an opposite side of said interior wall from said excretion inlet port.

8. A collection device according to claim 1 wherein said at least one interior wall extends at least 35% of a distance from said excretion inlet port to said rear wall.

9. A collection device according to claim 1 wherein said at least one interior wall extends at least 50% of a distance from said excretion inlet port to said rear wall.

10. A collection device for use in collecting patient excretions comprising:

a first hose comprising a first end and a second end;

a collection container comprising a substantially enclosed interior; an upper head portion comprising a forward portion; a rear, lower base portion comprising a rear wall; a vacuum port, an excretion inlet port, and a handle;

said excretion inlet port positioned in said forward portion of said upper head portion;

at least one interior wall extending within the interior of said substantially enclosed interior from said forward portion of said upper head portion and rearwardly at least 35% of a distance from said excretion inlet port to said rear wall, said interior wall forming an internal baffle between said excretion inlet port and said vacuum port;

a selectively openable and sealable sample access port for taking excretion samples from said interior;

said first end of said first hose connected to a vacuum source and said second end of said first hose connected to said vacuum port;

a collection wand comprising a rear hose connector and a forward inlet;

a second hose comprising a first end and a second end, said first end of said second hose connected to said excretion inlet port and said second end of said second hose connected to said rear hose connector of said collection wand; and a pivotal vacuum port plug positioned proximate said vacuum port, wherein said vacuum port plug moves to block said vacuum port when said collection device is rotated beyond a certain predetermined angle.

11. A collection device according to claim 10 wherein said lower base portion is wider than said forward portion.

12. A collection device according to claim 10 wherein said vacuum port is positioned higher than said base portion.

13. A collection device according to claim 10 wherein said vacuum port is positioned in said forward portion of said upper head portion on an opposite side of said interior wall from said excretion inlet port.

14. A collection device according to claim 13 wherein said at least one interior wall extends at least 50% of a distance from said excretion inlet port to said rear wall.

15. A collection device according to claim 10 wherein said at least one interior wall extends at least 50% of a distance from said excretion inlet port to said rear wall.

\* \* \* \* \*